United States Patent [19]
Lee et al.

[11] Patent Number: 6,077,933
[45] Date of Patent: Jun. 20, 2000

[54] REPRESSOR KRUPPEL-LIKE FACTOR

[75] Inventors: Mu-En Lee; Megan M. McA'Nulty, both of Newton, Mass.

[73] Assignee: President and Fellows of Harvard College, Cambridge, Mass.

[21] Appl. No.: 09/309,053

[22] Filed: May 10, 1999

Related U.S. Application Data

[62] Division of application No. 08/946,241, Oct. 7, 1997, Pat. No. 5,928,941
[60] Provisional application No. 60/030,035, Nov. 5, 1996, and provisional application No. 60/027,521, Oct. 7, 1996.
[51] Int. Cl.$^7$ .................................................. C07K 14/47
[52] U.S. Cl. .......................... 530/300; 530/324; 530/350
[58] Field of Search ..................................... 530/360, 324, 530/350

[56] References Cited

PUBLICATIONS

Shields et al, The Journal of Biological Chemistry, vol. 271 (33): pp. 20009–20017, Aug. 16, 1996.
Anderson et al., "Isolation of a Gene Encoding a Functional Zinc Finger Protein Homologous to Erythroid Kruppel–Like . . . ", Molecular & Cellular Biology 15:5957–5965, 1995.
Berg, "Zinc Fingers and Other Metal–binding Domains", The Journal of Biological Chemistry 265:6513–6516, 1990.
Bieker et al., "The Erythroid Kruppel–Like Factor Transactivation Domain is a Critical Component for Cell–Specific Inducibility of a β–Globin Promoter", Molecular & Cellular Biology 15:852–860, 1995.
Call et al., "Isolation and Characterization of a Zinc Finger Polypeptide Gene at the Human Chromosome 11 Wilms' Tumor Locus", Cell 60:509–520, 1990.
Crossley et al., "Regulation of the Erythroid Kruppel–like Factor (EKLF) Gene Promoter by the Erythroid Transcription Factor GATA–1*", The Journal of Biological Chemistry 269:15440–15444, 1994.
Donze et al., "Role of Erythroid Kruppel–like Factor in Human . . . ", the Journal of Biological Chemistry 270:1955–1959, 1995.
Fairall et al., "The Crystal Structure of a Two–Zinc–Finger Peptide Reveals an Extension to the Rules for Zinc–Finger/ DNA Recognition", Nature 366:483–487, 1993.
Feng et al., "Analysis of β–Thalassemia Mutant DNA Interactions with Erythroid Kruppel–Like Factor (EKLF), an Erythroid Cell–specific Transcription Factor", The Journal of Biological Chemistry 269:1493–1500, 1994.
Johnson, "The Price of Repression", Cell 81:655–658, 1995.
Maniatis et al., "Regulation of Inducible and Tissue–Specific Gene Expression", Science 236:1237–1245, 1987.
Miller et al., "A Novel, Erythroid Cell–Specific Murine Transcription Factor That Binds to the CACCC Element and Is Related to the Kruppel Family of Nuclear Proteins", Molecular & Cellular Biology 13:2776–2786, 1993.
Mitchell et al., "Transcriptional Regulation in Mammalian Cells by Sequence–Specific DNA Binding Proteins", Science 245:371–378, 1989.
Ptashne et al., "Activators and Targets", Nature 346:329–331, 1990.
Saha et al., "New Eukaryotic Trandscriptional Repressors", Nature 363:648–652, 1993.
Sanchez–Garcia et al., "The LIM Domain: A New Structural Motif Found in Zinc–Finger–Like Proteins", TIG 10:315–320, 1994.
Sauer et al., "Concentration–Dependent Transcriptional Activation or Repression by Kruppel From a Single Binding Site", Nature 353:563–566, 1991.
Sogawa et al., "cDNA Cloning and Transcriptional Properties of a Novel GC Box–binding protein, BTEB2", Nucleic Acids Research 21:1527–1532, 1993.
Tjian et al., "Transcriptional Activation: A Complex Puzzle with Few Easy Pieces", Cell 77:5–8, 1994.
Ward et al., "Repression of Promoters for the Mouse Insulin– like Growth Factor II–encoding Gene (IGF–2) by Products of the Wilms' Tumor Suppresssor gene Wt1", Gene 167:239–243, 1995.
Adams et al., Nature Genetics, vol. 4, pp. 373–380, Aug. 1993.
Nigo et al., The Protein Folding Problem and Tertiary Structure Prediction, Mertz et al (eds.), Birkhauser, Boston, pp. 443 and 492–495, 1994.

*Primary Examiner*—Terry McKelvey
*Attorney, Agent, or Firm*—Fish & Richardson, P.C.

[57] ABSTRACT

Disclosed is a novel mammalian protein designated repressor Krüppel-like factor (RKLF). RKLF is a zinc finger protein that binds to a CACCC element in DNA, thereby repressing gene transcription. An isolated DNA encoding RKLF, vectors and cells containing the DNA, and RKLF-specific antibodies are also disclosed. The RKLF DNA or protein can be introduced into the tissues of a mammal to inhibit neoplasia or hyperplasia. Also disclosed is an in vitro screening method for identifying a compound that induces RKLF gene expression.

4 Claims, 3 Drawing Sheets

```
   1 GGAATTCCGGGCGCAGGCCGGGACTCCGCGCCACGGCAGCCAGTCTCACCTGGCGGCACC
  61 GCCCGCCCACCGCCCCGGCCACAGCCCCTGCGCCCACGGCAGCACTCGAGGCGACCGCGA
 121 CAGTGGTGGGGACGCTGCTGAGTGGAAGAGAGCGCAGCCGGCCACCGGACCTACTTACT
 181 CGCCTTGCTGATTGTCTATTTTTGCGTTTACAACTTTTCTAAGAACTTTTGTATACAAAG
 241 GAACTTTTTAAAAAAGACGCTTCCAAGTTATATTTAATCCAAAGAAGAAGGATCTCGGCC
 301 AATTTGGGGTTTTGGGTTTTGGCTTCGTTTCTTCTCTTCGTTGACTTTGGGGTTCAGGTG
 361 CCCCAGCTGCTTCGGGCTGCCGAGGACCTTCTGGGCCCCCACATTAATGAGGCAGCCACC
   1                                                    M  R  Q  P  P
 421 TGGCGAGTCTGACATGGCTGTCAGCGACGCGCTGCTCCCATCTTTCTCCACGTTCGCGTC
   6  G  E  S  D  M  A  V  S  D  A  L  L  P  S  F  S  T  F  A  S
 481 TGGCCCGGCGGGAAGGGAGAAGACACTGCGTCAAGCAGGTGCCCCGAATAACCGCTGGCG
  26  G  P  A  G  R  E  K  T  L  R  Q  A  G  A  P  N  N  R  W  R
 541 GGAGGAGCTCTCCCACATGAAGCGACTTCCCCCAGTGCTTCCCGCCGGCCCCTATGACCT
  46  E  E  L  S  H  M  K  R  L  P  P  V  L  P  A  G  P  Y  D  L
 601 GGCGGCGGCGACCGTGGCCACAGACCTGGAGAGCGCCGGAGCCGGTGCGGCTTGCGGCGG
  66  A  A  A  T  V  A  T  D  L  E  S  A  G  A  G  A  A  C  G  G
 661 TAGCAACCTGGCGCCCCTACCTCGGAGAGAGACCGAGGAGTTCAACGATCTCCTGGACCT
  86  S  N  L  A  P  L  P  R  R  E  T  E  E  F  N  D  L  L  D  L
 721 GGACTTTATTCTCTCCAATTCGCTGACCCATCCTCCGGAGTCAGTGGCCGCCACCGTGTC
 106  D  F  I  L  S  N  S  L  T  H  P  P  E  S  V  A  A  T  V  S
 781 CTCGTCAGCGTCAGCCTCCTCTTCGTCGTCGCCGTCGAGCAGCGGCCCTGCCAGCGCGCC
 126  S  S  A  S  A  S  S  S  S  S  P  S  S  S  G  P  A  S  A  P
 841 CTCCACCTGCAGCTTCACCTATCCGATCCGGGCCGGGAACGACCCGGGCGTGGCGCCGGG
 146  S  T  C  S  F  T  Y  P  I  R  A  G  N  D  P  G  V  A  P  G
 901 CGGCACGGGCGGAGGCCTCCTCTATGGCAGGGAGTCCGCTCCCCCTCCGACGGCTCCCTT
 166  G  T  G  G  L  L  Y  G  R  E  S  A  P  P  P  T  A  P  F
 961 CAACCTGGCGGACATCAACGACGTGAGCCCCTCGGGCGGCTTCGTGGCCGAGCTCCTGCG
 186  N  L  A  D  I  N  D  V  S  P  S  G  G  F  V  A  E  L  L  R
1021 GCCAGAATTGGACCCGGTGTACATTCCGCCGCAGCAGCCGCAGCCGCCAGGTGGCGGGCT
 206  P  E  L  D  P  V  Y  I  P  P  Q  Q  P  Q  P  P  G  G  L
1081 GATGGGCAAGTTCGTGCTGAAGGCGTCGCTGAGCGCCCCTGGCAGCGAGTACGGCAGCCC
 226  M  G  K  F  V  L  K  A  S  L  S  A  P  G  S  E  Y  G  S  P
1141 GTCGGTCATCAGCGTCACGAAAGGCAGCCCTGACGGCAGCCACCCGGTGGTGGTGGCGCC
 246  S  V  I  S  V  T  K  G  S  P  D  G  S  H  P  V  V  V  A  P
1201 CTACAACGGCGGGCCGCCGCGCACGTGCCCCAAGATCAAGCAGGAGGCGGTCTCTTCGTG
 266  Y  N  G  G  P  P  R  T  C  P  K  I  K  Q  E  A  V  S  S  C
1261 CACCCACTTGGGCGCTGGACCCCCTCTCAGCAATGGCCACCGGCCGGCTGCACACGACTT
 286  T  H  L  G  A  G  P  P  L  S  N  G  H  R  P  A  A  H  D  F
1321 CCCCCTGGGGCGGCAGCTCCCCAGCAGGACTACCCCGACCCTGGGTCTTGAGGAAGTGCT
 306  P  L  G  R  Q  L  P  S  R  T  T  P  T  L  G  L  E  E  V  L
1382 GAGCAGCAGGGACTGTCACCCTGCCCTGCCGCTTCCTCCCGGCTTCCATCCCCACCCGGG
 326  S  S  R  D  C  H  P  A  L  P  L  P  P  G  F  H  P  H  P  G
1441 GCCCAATTACCCATCCTTCCTGCCCGATCAGATGCAGCCGCAAGTCCCGCCGCTCCATTA
 346  P  N  Y  P  S  F  L  P  D  Q  M  Q  P  Q  V  P  P  L  H  Y
1501 CCAAGAGCTCATGCCACCCGGTTCCTGCATGCCAGAGGAGCCCAAGCCAAAGAGGGGAAG
 366  Q  E  L  M  P  P  G  S  C  M  P  E  E  P  K  P  K  R  G  R
1561 ACGATCGTGGCCCCGGAAAAGGACCGCCACCCACACTTGTGATTACGCGGGCTGCGGCAA
 386  R  S  W  P  R  K  R  T  A  T  H  T  C  D  Y  A  G  C  G  K
1621 AACCTACACAAAGAGTTCCCATCTCAAGGCACACCTGCGAACCCACACAGGTGAGAAACC
 406  T  Y  T  K  S  S  H  L  K  A  H  L  R  T  H  T  G  E  K  P
1681 TTACCACTGTGACTGGGACGGCTGTGGATGGAAATTCGCCCGCTCAGATGAACTGACCAG
 426  Y  H  C  D  W  D  G  C  G  W  K  F  A  R  S  D  E  L  T  R
1741 GCACTACCGTAAACACACGGGGCACCGCCCGTTCCAGTGCCAAAAATGCGACCGAGCATT
 446  H  Y  R  K  H  T  G  H  R  P  F  Q  C  Q  K  C  D  R  A  F
1801 TTCCAGGTCGGACCACCTCGCCTTACACATGAAGAGGCATTTTTAAATCCCAGACAGTGG
 466  S  R  S  D  H  L  A  L  H  M  K  R  H  F  * (SEQ ID NO:9)
1861 ATATGACCCACACTGCCAGAAGAGAATTC (SEQ ID NO:1)
```

FIG. 1

```
RKLF  CDYAGCGKTYTKSSHLKAHLRTHTGEKPYH
EKLF  -GHE----S-S---------------A
LKLF  -S-TN----------------------
BTEB2 ---P--T-V-----------------K
Sp1   -HIQ----V-G-T---R----W----R-FM

RKLF  CDWDGCGWKFARSDELTRHYRKHTGHRPFQ
EKLF  -S----D-R-----------------C
LKLF  -N-E-----------------------
BTEB2 -T-E--D-R---------------AK---
Sp1   -T-SY--KR-T-----Q--K-T---EKK-A

RKLF  CQK..CDRAFSRSDHLALHMKRH (amino acids 389-469 of SEQ ID NO:2)
EKLF  -GL..-P---------------- (SEQ ID NO:10)
LKLF  -HL..------------------ (SEQ ID NO:11)
BTEB2 -GV..-N-S-------------- (SEQ ID NO:12)
Sp1   -PE..-PKR-M-----SK-I-T- (SEQ ID NO:13)
```

FIG. 2A

Identity of zinc finger region

|        | RKLF | EKLF | LKLF | BTEB2 |
|--------|------|------|------|-------|
| EKLF   | 83%  | ---  | ---  | ---   |
| LKLF   | 90%  | 82%  | ---  | ---   |
| BTEB2  | 82%  | 80%  | 80%  | ---   |
| Sp1    | 58%  | 59%  | 57%  | 60%   |

Identity of protein sequence

|        | RKLF | EKLF | LKLF | BTEB2 |
|--------|------|------|------|-------|
| EKLF   | 40%  | ---  | ---  | ---   |
| LKLF   | 52%  | 43%  | ---  | ---   |
| BTEB2  | 46%  | 41%  | 46%  | ---   |
| Sp1    | 28%  | 32%  | 25%  | 36%   |

REPRESSOR KRUPPEL-LIKE FACTOR

CROSS REFERENCE TO RELATED APPLICATION

This application is a divisional of and claims benefit from application Ser. No. 08/946,341, filed Oct. 7, 1977, now U.S. Pat. No. 5,928,941, which in turn claims benefit from provisional application Ser. No. 60/030,035 filed Nov. 5, 1996 and provisional application Ser. No. 60/027,521 filed Oct. 7, 1996.

STATEMENT AS TO FEDERALLY SPONSORED RESEARCH

This invention was made with Government support under grant number GM53249, awarded by the National Institutes of Health. The Government has certain rights in the invention.

BACKGROUND OF THE INVENTION

The invention relates to cell growth regulatory proteins.

Mammalian transcription factors regulate cellular processes such as cell lineage determination, cell growth and differentiation, and temporal or cell type-specific gene expression (Maniatis et al., 1987, *Science* 236:1237–1245; Mitchell et al., 1989, *Science* 245:371–378; Ptashne et al., 1990, *Nature* 346:329–331). Upon binding to specific cis-acting DNA sequences, transcription factors activate or repress transcription (Johnson, 1995, *Cell* 81:655–658; Tjian et al., 1994, *Cell* 77:5–8). Transcription factors are typically classified according to their DNA binding domains such as helix-loop-helix, leucine zipper, homeodomain, and zinc finger. The zinc finger transcription factors can be further classified into subfamilies based on amino acids important for zinc binding (e.g., Cys2His2, Cys4, or Cys3His1), spacing between the zinc binding amino acids, and transcription activation or repression domain (e.g., glutamine rich, acidic amino acid rich, or proline rich domain).

The erythroid Krüppel-like factor (EKLF) subfamily includes zinc finger proteins, such as erythroid (EKLF) and lung (LKLF) Krüppel-like factors, and BTEB2 (or placental Krüppel-like factor). These proteins are preferentially expressed in certain mammalian tissues, where they transactivate gene expression upon binding to DNA. This subfamily is characterized by a highly conserved C-terminal region (more than 80% conserved) containing three Cys2His2 zinc fingers and a proline rich N-terminal domain (Anderson et al., 1995, *Mol. Cell. Biol.* 15:5957–5965; Donze et al., 1995, *J. Biol. Chem.* 270:1955–1959; Miller et al., 1993, *Mol. Cell. Biol.* 13:2776–2786; Sogawa et al., 1993, *Nucl. Acids Res.* 21:1527–1532). EKLF is essential for the expression of the β-globin gene in mice. The zinc fingers of EKLF bind a CACCC regulatory element of the β-globin promoter.

SUMMARY OF THE INVENTION

A novel protein, designated repressor Krüppel-like factor (RKLF), is identified and characterized. This protein is preferentially expressed in normal cells of the colon, small intestine, and lung, but nor in neoplastic cells or hyperplastic cells. RKLF contains three Krüppel-like zinc fingers. RKLF binds specifically to a CACCC consensus sequence (CACCC element) in DNA and represses transcription of a gene having a CACCC element operably linked to its promoter.

The invention includes an isolated DNA containing a nucleotide sequence that encodes an RKLF protein that binds to a CACCC element in a DNA, thereby repressing transcription of a gene operably linked to the CACCC element. The RKLF protein encoded by the DNA of the invention shares at least 80% sequence identity with SEQ ID NO:2. Preferably, the isolated DNA includes a nucleotide sequence that defines a DNA molecule whose complement hybridizes under stringent hybridization conditions to a DNA having a nucleotide sequence consisting essentially of SEQ ID NO:1. Preferably the isolated DNA encodes a naturally occurring mammalian RKLF. More preferably, the DNA includes the coding sequence of SEQ ID NO:1 (human RKLF cDNA), or of a degenerate variant of SEQ ID NO:1.

The invention also includes a vector containing the above-described DNA, and a cell containing such a vector. The cell can be prokaryotic or eukaryotic e.g., an animal cell such as a mammalian cell. Preferably, the cell expresses the protein encoded by SEQ ID NO:1.

The invention also includes a substantially pure RKLF protein which shares at least 80% sequence identity with SEQ ID NO:2 and binds to a CACCC element in a DNA molecule, thereby repressing transcription of a gene operably linked to the CACCC element. Preferably, the sequence identity shared with SEQ ID NO:2 is at least 85%. More preferably, the sequence identity is at least 90%, and most preferably it is at least 95%. Preferably, the amino acid sequence of the RKLF protein differs from SEQ ID NO:2 solely by conservative amino acid substitutions, i.e., substitution of one amino acid for another of the same class, or by non-conservative substitutions, deletions, or insertions located at positions that do not destroy the function of the protein. Preferably, the RKLF protein is a naturally occurring mammalian protein. More preferably, it is a human protein. Most preferably, the RKLF protein includes the amino acid sequence of SEQ ID NO:2 (human RKLF). Also included in the invention is any naturally occurring homolog or isoform of SEQ ID NO:2.

The invention also includes an RKLF-specific antibody, which can be polyclonal or monoclonal. The antibody can be conjugated to a detectable label.

The invention also includes a method for inhibiting neoplasia in a mammal. In the method, the above-described DNA can be introduced into neoplastic cells in a mammal. Preferably, the RKLF DNA is incorporated into an expression vector for introduction into the neoplastic cells. Alternatively, to inhibit neoplasia in a mammal, RKLF protein can be directly introduced into neoplastic cells.

The invention also includes a method for inhibiting hyperplasia in a mammal. In the method, the above-described DNA can be introduced into hyperplastic cells in a mammal, or into cells at risk of becoming hyperplastic in a mammal. Preferably, the RKLF DNA is incorporated into an expression vector for introduction into the cells. Alternatively, RKLF protein can be introduced directly into hyperplastic cells in a mammal, or into cells at risk of hyperplasia.

The invention also includes an in vitro screening method for identifying a compound that induces RKLF gene expression. The screening method includes the steps of: (a) providing a test cell; (b) contacting the test cell with a candidate compound; and (c) detecting an increase in the level of RKLF gene expression in the presence of the candidate compound, compared to the level of RKLF expression in the absence of the candidate compound.

As used herein, "high stringency" means the following DNA hybridization and wash conditions: hybridization at 42° C. in the presence of 50% formamide; a first wash at 65° C. with 2×SSC containing 1% SDS; followed by a second wash at 65° C. with 0.1×SSC.

As used herein, "hyperplasia" means an increase in the number of cells in a tissue or organ, excluding tumor formation and excluding normal growth, whereby the bulk of the tissue or organ is increased. A well known example of hyperplasia is neointimal hyperplasia. In that process, the intimal layer of a traumatized (e.g., by surgery) artery increases in thickness, thereby narrowing the arterial lumen. A cell at risk of becoming hyperplastic is a cell subjected to, or about to be subjected to a known risk factor for hyperplasia, which cell does not yet exhibit hyperplasia. For example, immediately before, during, or immediately after a procedure such as balloon angioplasty or surgery on an artery, intimal cells in that artery are at risk of hyperplasia.

As used herein, "isolated DNA" means DNA free of the genes that flank the gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Also included is a recombinant DNA that includes a portion of SEQ ID NO:1 and that encodes an alternative splice variant of RKLF.

As used herein, "neoplasia" means a pathological process that results in the formation and growth of a benign or malignant tumor. Typically, neoplastic cells proliferate more rapidly than surrounding cells and continue to grow after the stimulus that initiated the new growth ceases.

As used herein, "operably linked" means incorporated into a genetic construct so that expression control sequences effectively control expression of a gene of interest.

As used herein, "protein" means any peptide-linked chain of amino acids, regardless of length or post-translational modification, e.g., glycosylation or phosphorylation.

As used herein, "RKLF protein" means a protein that shares at least 80% amino acid sequence identity with SEQ ID NO:2, and binds to a CACCC element in a DNA molecule, thereby repressing transcription of a gene operably linked to the CACCC element.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

As used herein, "substantially pure protein" means a protein separated from components that naturally accompany it. Typically, the protein is substantially pure when it is at least 60%, by weight, free from the proteins and other naturally-occurring organic molecules with which it is naturally associated. Preferably, the purity of the preparation is at least 75%, more preferably at least 90%, and most preferably at least 99%, by weight. A substantially pure RKLF protein can be obtained, for example, by extraction from a natural source, by expression of a recombinant nucleic acid encoding an RKLF polypeptide, or by chemical synthesis. Purity can be measured by any appropriate method, e.g., column chromatography, polyacrylamide gel electrophoresis, or HPLC analysis. A chemically synthesized protein or a recombinant protein produced in a cell type other than the cell type in which it naturally occurs is, by definition, substantially free from components that naturally accompany it. Accordingly, substantially pure proteins include those having sequences derived from eukaryotic organisms but synthesized in *E. coli* or other prokaryotes.

As used herein, "test cell" means a cell containing an RKLF gene operably linked to expression control sequences, in which cell RKLF gene expression is low or nondetectable in the absence of an RKLF inducer. Preferably, the expression control sequences include a promoter that is naturally associated with an RKLF gene.

As used herein, "vector" means a replicable nucleic acid construct, e.g., a plasmid or viral nucleic acid.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

BRIEF DESCRIPTION OF THE DRAWINGS

FIG. 1 is the nucleotide sequence a human RKLF cDNA (SEQ ID NO:1) and the deduced amino acid sequence of human RKLF protein (SEQ ID NO:9). The three zinc finger domains are underlined. Proline residues are indicated in bold typeface.

DETAILED DESCRIPTION

Expression Control Sequences and Vectors

The RKLF DNA of this invention can be used in a form of therapy to inhibit neoplasia or hyperplasia in a mammal, or to produce recombinant RKLF protein. For such uses, the RKLF DNA is typically cloned into an expression vector, i.e., a vector wherein RKLF DNA is operably linked to expression control sequences. The need for, and identity of, expression control sequences will vary according to the type of cell in which the RKLF DNA is to be expressed. Generally, expression control sequences include a transcriptional promoter, enhancer, suitable mRNA ribosomal binding sites, and sequences that terminate transcription and translation. Suitable expression control sequences can be selected by one of ordinary skill in the art. Standard methods can be used by the skilled person to construct expression vectors. See generally, Sambrook et al., 1989, *Molecular Cloning: A Laboratory Manual* (2nd Edition), Cold Spring Harbor Press, N.Y. Vectors useful in this invention include plasmid vectors and viral vectors. Preferred viral vectors are those derived from retroviruses, adenovirus, adeno-associated virus, SV40 virus, or herpes viruses.

RKLF DNA In Vitro

In some embodiments of the invention, RKLF DNA is introduced into, and expressed in, a prokaryotic cell. A preferred prokaryotic cell is *Escherichia coli*. For expression in a prokaryotic cell, RKLF DNA can be integrated into a bacterial chromosome or expressed from an extrachromosomal DNA.

In other embodiments of the invention, the RKLF DNA is introduced into, and expressed in, a eukaryotic cell in vitro. Eukaryotic cells useful for expressing RKLF DNA in vitro include, but are not limited to, COS, CHO, and Sf9 cells. Transfection of the eukaryotic cell can be transient or stable. The RKLF DNA can be, but is not necessarily, integrated into a chromosome of the eukaryotic cell.

RKLF DNA In Vivo

When RKLF DNA is used to inhibit neoplasia or hyperplasia in a mammal, the RKLF DNA is introduced into cells or tissues of the mammal in vivo. In preferred embodiments of the invention, RKLF DNA is used to inhibit neointimal hyperplasia in an artery of a mammal. In such preferred embodiments, the RKLF DNA typically is introduced into cells lining the an artery of a mammal, e.g., before or after surgery or angioplasty.

Various methods for introducing DNA into mammalian tissues are known and can be used by a skilled person in the practice of this invention. Cells in intact tissue take up naked DNA. For example, mammalian muscle cells have been shown to take up naked DNA dissolved in aqueous solution and injected into muscle tissue. Preferably, however, RKLF DNA is introduced into mammalian tissues by means of a vector, (e.g., a retrovirus) or vehicle (e.g., liposomes) to improve uptake efficiency. The selection and use of a suitable vector or vehicle for introducing RKLF DNA into mammalian tissues is within ordinary skill in the art. Examples of DNA uptake vectors and vehicles that car be used in this invention include those described below.

Direct transfer of RKLF DNA into intact mammalian tissues, e.g., vascular tissue, can be carried out by means of cationic lipids (Lim et al., 1991, *Circulation* 83:2007–2011; Lynch et al., 1992, *Proc. Natl. Acad. Sci. USA* 89:1138–1142; Flugelman et al., 1992, *Circ. Res.* 70:348–354). An exemplary cationic lipid is commercially available as Lipofectin™ (GIBCO/BRL). Another commercial lipid for introduction of DNA into cells is Liposin™. RKLF DNA-containing liposomes or vectors can be introduced into an artery by means such as a double balloon catheter (Nabel et al., 1990, *Science* 244:1285–1288).

Endothelial cells transfected with RKLF DNA in a retroviral construct can be used to introduce DNA into vascular tissue of a mammal (Nabel et al., 1989, *Science* 244:1342–1344). Vascular grafts seeded with endothelial cells transfected with RKLF DNA inserted into a retrovirus can be used to transfer DNA into vascular walls (Wilson et al., 1989, *Science* 244:1344–1346). Hemagglutinating virus of Japan (HVJ; also called Sendai virus) can be used to deliver an RKLF DNA into a mammalian vascular tissue in vivo (Dzau et al., 1993, *TIBTECH* 11:205–210; Morishita et al., 1993, *Proc. Natl. Acad. Sci. USA* 90:8474–8478). A method for topical delivery of RKLF DNA, e.g., to the adventitial layer of an artery in a mammal, is the pluronic gel method (Simons et al., 1992, *Nature* 359:67–70).

The foregoing methods for introducing RKLF DNA into mammalian cells or tissues in vivo to inhibit hyperplasia can also be used to introduce RKLF DNA into mammalian cells in vivo, to inhibit neoplasia.

RKLF-Specific Antibodies

The RKLF-specific antibody of the invention can be polyclonal or monoclonal. Standard protocols for monoclonal and polyclonal antibody production are known and can be carried out by one of ordinary skill in the art, to obtain antibodies useful in this invention. Preferably, the RKLF antibody binds to an RKLF epitope that is not part of the RKLF zinc finger domain. The antibody can be used, for example, to purify the RKLF protein.

The invention encompasses not only an intact monoclonal antibody, but also an immunologically active antibody fragment. Examples of such a fragment include a Fab or (Fab)$_2$ fragment, an engineered single chain Fv molecule, or a chimeric antibody (such as a "humanized" antibody). Typically, a chimeric antibody includes a variable region of a non-human antibody, e.g., a murine variable region, and a constant region of a human antibody.

In some embodiments of the invention, an antibody or antibody fragment is linked to a detectable label. Examples of detectable labels include a radioactive label, a nonradioactive isotopic label, a fluorescent label, an enzyme label, and a colorimetric label.

Cloning of RKLF cDNA

A cDNA probe encoding the c-terminal zinc finger region of EKLF (bp 895–1146) was generated by reverse transcription PCR (Lee et al., 1991, *J. Biol. Chem.* 266:16188–92; Sambrook et al., supra. The forward primer had the following sequence: 5' GAACTTTGC ACCTAAGACG CAG 3' (SEQ ID NO:3), and the sequence of the reverse primer was: 5' ACGCTTCATG TGCAGAGCTA AGTG 3' (SEQ ID NO:4). These primers were designed according to the published sequence of EKLF (Miller et al., 1993, *Mol. Cell Biol.* 13:2776–86). The resulting DNA fragment was labeled by random priming and used as a probe to screen a human fetal heart library in λgt11 (Clontech, Palo Alto, Calif.).

Approximately 1.6 million phage particles were plated, transferred to nitrocellulose, and screened according to standard techniques. The filters were washed initially with 0.5×SSC, 0.1% SDS at 37° C. and then more stringently with 0.2×SSC, 0.1% SDS at 65° C. More than 40 clones were obtained. Six clones were isolated, and three were sequenced. One of those included the entire human RKLF coding sequence. The cDNAs were mapped by restriction digestion and sequenced from both orientations at least once, by the dideoxy chain termination method or by using an automated DNA Sequencer (Licor, Lincoln, Nebr.) according to the manufacturer's instructions. Sequence analysis was performed using the GCG software package (Genetics Computer Group, Madison, Wis.).

In Vitro Transcription and Translation

The cDNA containing the entire human RKLF coding sequence was cloned into the eukaryotic expression vector pCDNA3 (Invitrogen, San Diego). In vitro transcription and translation were carried out using the TNT-coupled reticulocyte extract system (Promega, Madison, Wis.) according to the manufacturer's instructions. The transcribed and translated products were resolved on a 10% SDS-PAGE gel and visualized by autoradiography, using Kodak BMR film at room temperature.

Northern Blot Analysis

Rat tissues were obtained from adult male Sprague-Dawley rats (Charles River, Wilmington, Mass.). Total RNA from rat tissue was purified by a standard guanidinium/CsCl ultracentrifugation technique (Sambrook et al., supra). Total RNA from the skeletal muscle and ventricles of a 21-week-old human fetus was prepared by guanidinium/CsCl ultracentrifugation. (The use of this tissue was approved by the Human Research Committee of the Brigham and Women's Hospital, Boston.) Total RNA from adult human tissue was obtained commercially (Clontech, Palo Alto, Calif.).

RNA was fractionated on a 1.3% formaldehyde-agarose gel and transferred to nitrocellulose filters. The filters were hybridized with a [$^{32}$P]dCTP-labeled, random-primed rat or human RKLF cDNA probe (Hsieh et al., 1996, *J. Biol. Chem.* 271:17354–59; Jain et al., 1996, *J. Biol. Chem.* 271:10194–10199). The rat RKLF probe was generated by reverse transcription PCR, using rat colon RNA and primers designed according to the sequence of the human RKLF cDNA (SEQ ID NO:1). The 5' primer was based on nucleotides 416–435 of SEQ ID NO:1. The 3' primer was based on the complement of nucleotides 1028–1048 of SEQ ID NO:1.

Following the hybridization reaction, filters were washed in 0.2×SSC (30 mM sodium chloride, 3 mM sodium citrate, and 0.1% SDS) at 55° C. They were then exposed to Kodak XAR film at −80° C. To correct for differences in RNA loading, the blots were hybridized with an 18S rRNA oligonucleotide probe. The filters were also exposed to phosphor screens. Radioactivity was measured with a PhosphorImager™ using the ImageQuant™ software (Molecular Dynamics, Sunnyvale, Calif.).

In Situ Hybridization

Rat RKLF mRNA was detected in situ essentially as described by Lee et al. (1993, *Endocrinology* 132:2136–2140). A 633 bp rat RKLF cDNA fragment (used for Northern analysis) was cloned into the pCRII vector. Labeled ($^{35}$S-UTP) antisense and sense cRNA were synthesized with T7 and SP6 polymerase, respectively. In situ hybridization was carried out with [$^{32}$P]UTP labeled sense or antisense cRNA probes on tissue sections at 50° C. After hybridization, the tissue sections were washed under moderately stringent conditions. Dried tissue sections were subjected to autoradiography, using Kodak NTB2 emulsion (Eastman Kodak., Rochester, N.Y.) for 6 to 9 days at 4° C.

Specific RKLF signal was observed in the slides hybridized with antisense riboprobe. Hybridization with RKLF sense riboprobe was performed to control for nonspecific hybridization background. Counterstaining was performed with hematoxylin and eosin.

GST-RKLF Fusion Protein

A cDNA fragment containing the coding region of RKLF, except the first 10 amino acids (bp 437–1889 of SEQ ID NO:1), was amplified by PCR. The fragment was inserted into the BamH1 and EcoR1 sites of the GST-fusion vector pGEX-2T (Pharmacia Biotech Inc., Piscataway, N.J.). The GST-RKLF fusion protein was produced in *E. coli* and purified with glutathione sepharose 4B according to the manufacturer's instructions. The protein was analyzed by a 10% SDS-PAGE gel before use in the gel-shift assay.

Gel Mobility Shift Assay

The assay was performed with purified GST-RKLF fusion protein and radiolabeled probes. The probes were made from double stranded oligonucleotides synthesized according to the sequence of the CACCC site of the β-globin promoter (5' AGCTAGCCAC ACCCTGAAGCT 3'; SEQ ID NO:5) and radiolabeled (Yoshizumi et al., 1995, *Mol. Cell. Biol.* 15:3266–3272). Binding conditions were essentially as described for EKLF (Feng et al., 1994, *J. Biol. Chem.* 269:1493–1500; Miller et al., 1993, *Mol. Cell Biol.* 13:2776–2786). A typical binding reaction mixture contained 20,000 cpm of probe, 0.5 µg of GST-RKLF, 1 µg of poly(dI-dC)•poly(dI-dC), 25 µM HEPES, pH 7.5, 16 mM KCl, 50 mM NaCl, 2 µM ZnCl$_2$, 0.6 mM β-mercaptoethanol, and 8% glycerol. The probe and protein were incubated on ice for 20 minutes and analyzed by a 5% polyacrylamide gel in 0.5×TBE buffer (44 mM Tris base, 44 mM boric acid, 1 mM EDTA). The sequences of the mutant and the non-identical competitor oligonucleotides were 5' AGCTAGCCAC ACCGTGAAGCT 3' (SEQ ID NO:6) and 5' GACCGTGGCA CAGACTGGAG 3' (SEQ ID NO:7), respectively.

Transient Co-Transfection Assay

Plasmids pSG5-RKLF and pSG5-RKLF(AS) were constructed by inserting the full-length human RKLF cDNA into the EcoRI site of the eukaryotic expression plasmid pSG5 (Stratagene, La Jolla, Calif.) in sense and antisense orientations, respectively. To generates plasmid pSG5-RKLF (ΔZn), a cDNA fragment coding for bp 32 to 1554 of the human RKLF cDNA was amplified. This DNA fragment contained most of the open reading frame except the C-terminal zinc finger region. This DNA fragment was cloned into PCRII (Invitrogen, San Diego, Calif.) and the open reading frame of this DNA fragment was confirmed by sequencing and in vitro transcription and translation. After confirmation, the DNA fragment was cloned into the EcoR1 site of pSG5. The reporter plasmid pCAC-tkCAT and the expression plasmid pSG5-EKLF were provided by Dr. J. J. Bieker (New York, N.Y.). Plasmid DNA used in transient transfection assays was isolated by alkaline lysis followed by CsCl equilibrium centrifugation (Sambrook et al., supra).

Transient transfection assays were performed in bovine aortic endothelial cells (BAEC) because they did not express a detectable level of RKLF. BAEC were isolated and cultured in Dulbecco's modified Eagle's with 10% fetal calf serum, antibiotics, and L-glutamine (JRH Biosciences, Lenexa, Kans.) (Lee et al., 1990, *J. Biol. Chem.* 265:10446–10450; Yoshizumi et al., 1995, *Mol. Cell. Biol.* 15:3266–3272). Passages 5–6 of BAEC were transfected using the calcium phosphate method. Six μg of reporter plasmid pCAC-tkCAT and 12 μg of pSG5-EKLF or equimolar of pSG5-RKLF or pSG5 expression plasmid, were used in these transfection experiments. To correct for variability in transfection efficiency, 1 μg of pCMV-βGAL (containing the potent CMV enhancer and promoter driving the structural gene coding for β-galactosidase) was cotransfected in all experiments.

Forty eight hours after transfection, cell extracts were prepared in reporter lysis buffer (Promega, Madison, Wis.) according to the manufacturer's specifications. Chloramphenicol acetyl transferase (CAT) and β-galactosidase assays were performed. The ratio of CAT activity to β-galactosidase activity in each sample served as a measure of normalized luciferase activity. Each construct was transfected at least three times, and each transfection was done in triplicate. Data for each construct are presented as mean±SE.

Human RKLF cDNA

The sequence in FIG. 1 reveals potential open reading frames beginning at each of two in-frame methionine codons (amino acids 1 and 10). The longest open reading frame, beginning with the first methionine, would encode a protein containing 479 amino acids (SEQ ID NO:9). However, the first methionine codon is flanked by a poor match to the Kozak consensus sequence for translation initiation (Kozek, 1992, *Ann. Rev. Cell Biol.* 8:197–225). The nucleotide sequence flanking the second methionine codon complies with the Kozak consensus sequence. Therefore, the major protein product apparently begins with the second methionine and contains 470 amino acids (SEQ ID NO:2). The calculated molecular weight of the major human RKLF protein (SEQ ID NO:2) is 50 kDa. This protein has an estimated pI of 9.21.

In vitro transcription and translation was used to confirm the amino terminus of the RKLF expression product. The in vitro transcription and translation was performed by using an expression plasmid pcDNA3, containing the full-length RKLF cDNA. The major translated product had an apparent molecular weight of 60 kDa, higher than the predicted molecular weight of the 470 amino acid RKLF protein (SEQ ID NO:2). The difference between the predicted and actual molecular weight of RKLF is explained, at least in part, by its high proline content.

Comparison of Human RKLF with Other Zinc Finger Proteins

Figure 2A:
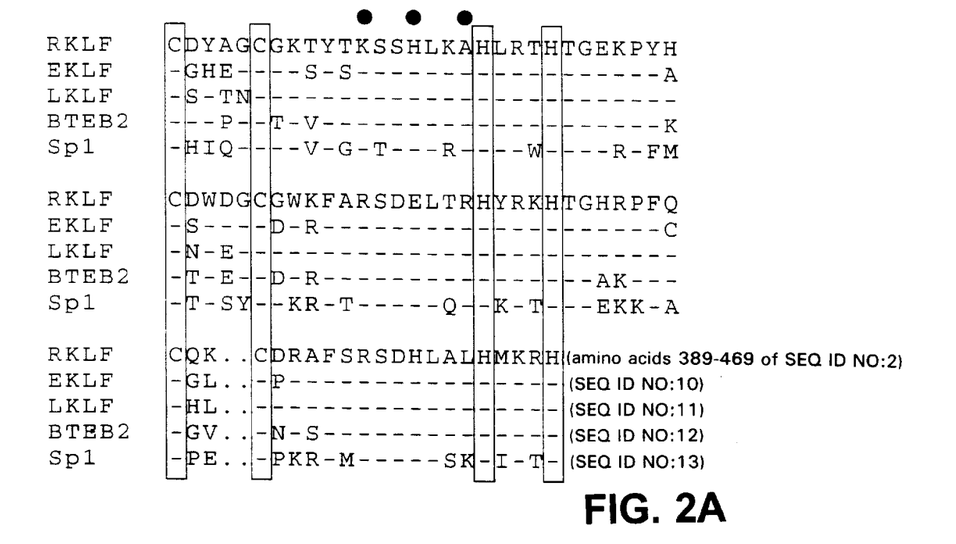
FIGS. 2A–2B are charts aligning and comparing amino acid sequences of the zinc finger domains of human RKLF and other zinc finger proteins. The zinc finger domains are aligned according to positions of cysteine and histidine residues. These residues are shown in boxes. The residues predicted to contact DNA according to the model of Klevit (1991, *Science* 253:1367–1393) are indicated by a dot. Dashes indicate sequence positions identical in RKLF. EKLF amino acid sequence GHESSASDRCGLP is SEQ ID NO:10; LKLF amino acid sequence STNNEHL is SEQ ID NO:11; BTEB amino acid sequence PTVKTEDRAKGVNS is SEQ ID NO:12; and Sp1 amino acid sequence HIQVGTRWRFMTSYKRTQKTEKKAPEPKRMSKIT is SEQ ID NO:13.
Figure 2B:
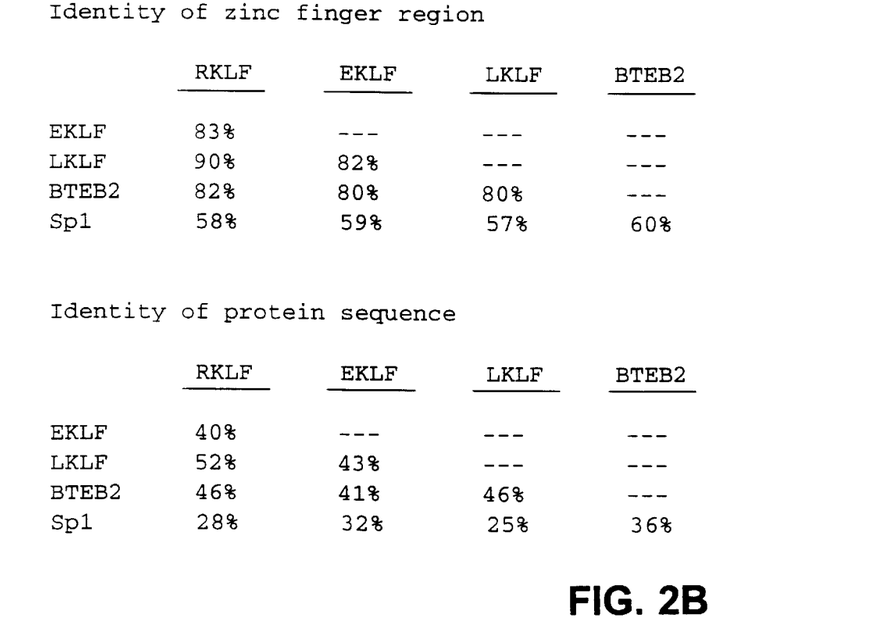
Figure 3:
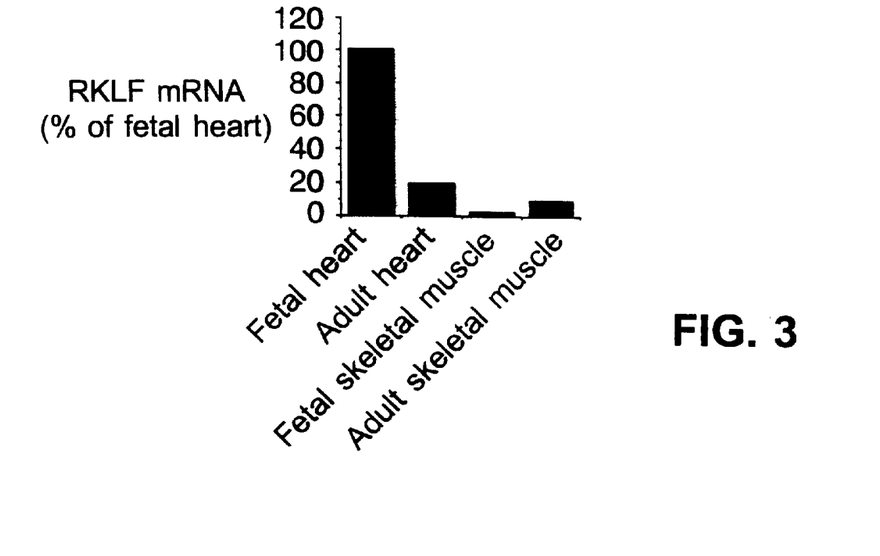
FIG. 3 is a bar graph summarizing data on RKLF mRNA levels in fetal and adult rat heart tissue, and fetal and adult rat skeletal muscle tissue. Northern analysis was performed with 20 μg of total RNA from the indicated tissue. The fetal RNA was isolated from a 21 week old fetus. The adult RNA was supplied by Clontech. After electrophoresis, RNA was transferred to nitrocellulose and hybridized with a $^{32}$P-labeled rat RKLF cDNA probe and a 18S probe. To correct for differences in loading, the signal density of each RNA sample hybridized to the RKLF probe was divided by that hybridized to the 18S probe. The corrected density was then plotted as a percentage of the fetal heart.

Analysis of the amino acid sequence of human RKLF (SEQ ID NO:2) revealed three Cys2His2 Krüppel-type fingers at the C-terminal (Fig. h.s. 1). An amino acid alignment of the RKLF zinc finger region with EKLF, LKLF, BTEB2, and SP1 is shown in FIG. 2. The zinc binding residues (boxed), the number of amino acids between the boxed residues, and the three amino acids (marked by dots) that have been shown to contact DNA in other Cys2His2 fingers (Fairall et al., 1993, *Nature* 366:483–487; Klevit, 1991, *Science* 253:1367–1393) are completely conserved.

Outside the zinc finger region, the amino acid sequence diverges between RKLF and the rest of the EKLF family. The overall identity (including the zinc finger region) among family members is low (FIG. 2).

Tissue and Cellular Distribution of RKLF

Using reverse transcription PCR, a 633 bp rat RKLF cDNA fragment outside of the zinc finger coding region was amplified. The rat RKLF is ~90% identical to the human homologue at the nucleotide level. Total RNA was extracted from 10 adult rat tissues and analyzed by Northern blot analysis using the rat RKLF probe. A single intense 3.0 kb message was detected in both colon and small intestine. RKLF was also expressed highly in the lung and at a lower level in the aorta. This expression pattern is distinct from that of other members of the EKLF family (Anderson et al., 1995, *Mol. Cell. Biol.* 15:5957–5965; Miller et al., 1993, *Mol. Cell. Biol.* 13:2776–2786; Sogawa et al., 1993, *Nucl. Acids Res.* 21:1527–1532).

In situ hybridization was used to identify the cell types expressing RKLF in rat colon. For each antisense experiment with the rat RKLF riboprobe, a corresponding sense (control) experiment was performed. Compared with the background signal of the sense probe, hybridization of rat colon with the RKLF antisense probe showed intense signal in the more mature epithelial cells in the apex of villi. In contrast, RKLF mRNA was undetectable in immature proliferating cells at the base of colonic crypts. There was no detectable expression of RKLF in the visceral smooth muscle cells of the submucosa and muscularis mucosae. Although in situ hybridization was not done using tissue from the lung or aorta, RKLF mRNA has been detected in mink lung epithelial cells and rat aortic smooth muscle cells in culture. RKLF mRNA was undetectable in human umbilical vein endothelial cells, human aortic endothelial cells, and bovine aortic endothelial cells.

Developmental Regulation of RKLF mRNA in Human Heart

RKLF was isolated from a fetal heart library. In adult rat heart, however, RKLF mRNA was barely detectable. To determine whether the expression of RKLF is regulated developmentally in the heart, we performed Northern analysis using total RNA isolated from heart and skeletal muscle of a 21-week old human fetus and a human adult. The size of the human RKLF message was similar to that of the rat homologue. Human RKLF was expressed at a low level in terminally differentiated adult heart tissue. The level of RKLF mRNA was 5-fold higher in the fetal heart. Very low levels of RKLF message were detected in both human fetal and adult skeletal muscle.

Binding of RKLF to CACCC Element of β-Globin Gene

The sequence conservation among the zinc finger regions of RKLF, EKLF, and LKLF suggested that RKLF would bind the CACCC element. This was confirmed experimentally.

For this experiment, a GST-RKLF fusion protein containing the entire RKLF protein except the first 10 amino acids was produced. Gel mobility shift analysis was then performed using the GST-RKLF fusion protein and an oligonucleotide probe encoding the CACCC element of the β-globin gene (Miller et al., 1993, *Mol. Cell. Biol.* 13:2776–2786). GST protein was used as a negative control. Incubation of GST-RKLF but not GST protein with the probe resulted in a DNA-protein complex. This complex resulted from specific binding, because it was competed away by unlabeled identical probe in a dose dependent manner but not by probe encoding an unrelated sequence. An unlabeled probe with a mutation in the CACCC site (CACCG) failed to compete away the binding.

RKLF Represses Transcription by Binding to CACCC Element

The ability of RKLF to use a single copy of the β-globin CACCC site to transactivate or repress a CAT reporter plasmid (CAC-tkCAT) that contains the minimal thymidine kinase promoter activity was tested.

Figure 4:
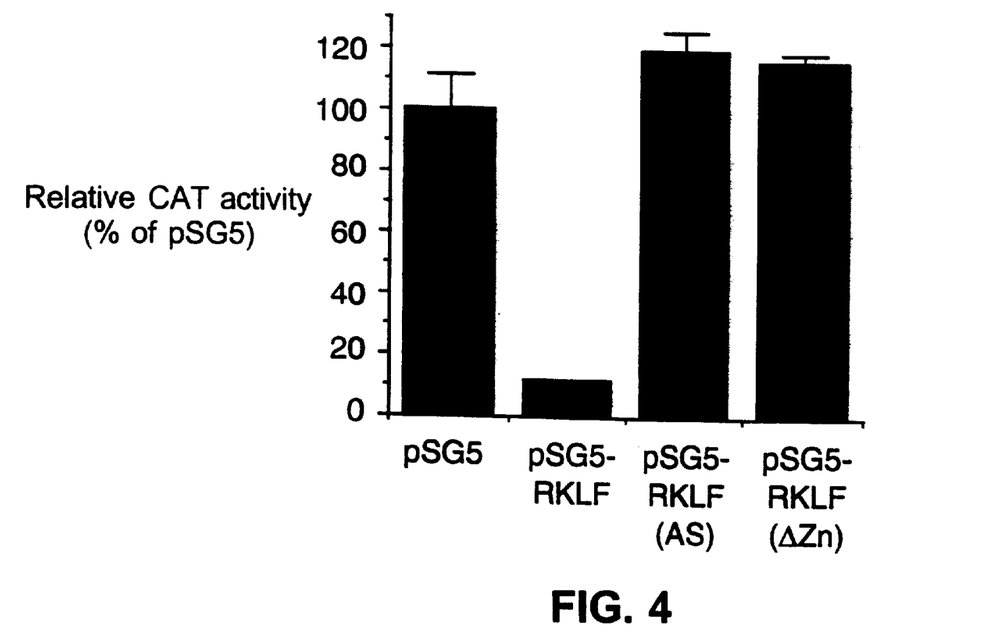
FIG. 4 is a bar graph summarizing data from cotransfection experiments of a CACCC element-containing reporter plasmid (pCAC-tkCAT) and RKLF expression plasmids (pSG5-RKLF, pSG5-RKLF(AS), pSG5-RKLF(ΔZn)) in bovine aortic endothelial cells. The levels of CAT and β-galactosidase activities in cell extracts were determined. For each construct, the plasmid pCMV-βGAL was cotransfected to correct for differences in transfection efficiency. Plasmid pSG5 was used as a negative control. The relative CAT activities were expressed as a percentage of the pSG5 expression vector (mean±SE).

A full-length human RKLF cDNA was cloned into the eukaryotic expression plasmid pSG5 in both orientations, to obtain the sense and antisense plasmids pSG5-RKLF and pSG5-RKLF(AS), respectively. BAEC were chosen for transfection experiments because they do not express RKLF or EKLF. As a positive control, CAC-tkCAT, and pSG5-EKLF (EKLF expression vector) were cotransfected. Cotransfection of pSG5-EKLF markedly increased the CAT activity, as expected (Miller et al., supra). In contrast, cotransfection of pSG5-RKLF decreased the promoter activity of CAC-tkCAT by 90% (FIG. 4). This repression was specific, because cotransfection of the antisense plasmid pSG5-RKLF(AS) had no effect. In addition, cotransfection of plasmid pSG5-RKLF(ΔZn), that expressed a truncated RKLF without the C-terminal zinc finger region, also failed to repress the promoter activity of CAC-tkCAT (FIG. 4). Furthermore, pSG5-RKLF did not decrease promoter activity if the CACCC site was deleted in plasmid CAC-tkCAT. These results demonstrate that RKLF is a transcriptional repressor, unlike other members of the EKLF family. These results indicate that the RKLF repressor activity depends on RKLF binding to the CACCC element.

RKLF Tissue Distribution

RKLF was found to be preferentially expressed in rat colon, small intestine, and lung, with a lower level of expression in the aorta. In the colon, RKLF was expressed in epithelial cells. By in situ hybridization, the expression of RKLF mRNA was detected in relatively mature cells in the apex of colonic villi, but not in the immature, proliferating cells in colonic crypt.

Deposit Statement

The subject cultures have been deposited under conditions that assure that access to the cultures will be available during the pendency of the patent application disclosing them to one determined by the Commissioner of Patents and Trademarks to be entitled thereto under 37 CFR 1.14 and 35 USC 122. The date of deposit was: Nov. 5, 1996. The ATCC accession number is 98236. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Other embodiments are within the following claims.

---

What is claimed is:

1. A substantially pure protein whose amino acid sequence is SEQ ID NO:2.

2. A substantially pure protein that includes a domain consisting of amino acids 389–469 of SEQ ID NO:2, or amino acids 389–469 with one or more conservative amino acid substitutions therein, provided that amino acids 389, 394, 419, 424, 449 and 452 remain as cysteine residues, and amino acids 407, 411, 437, 441, 465 and 469 remain as histidine residues, wherein said protein binds to a CACCC element in a DNA molecule.

3. A substantially pure protein whose amino acid sequence is SEQ ID NO:2 with one or more conservative amino acid substitutions therein.

4. A substantially pure protein comprising amino acids 389–469 of SEQ ID NO:2, wherein said protein binds to a CACCC element in a DNA molecule and represses transcription of a gene operably linked to said CACCC element.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 1889 base pairs
        (B) TYPE: nucleic acid
        (C) STRANDEDNESS: single
        (D) TOPOLOGY: linear     (ix) FEATURE:
        (A) NAME/KEY: Coding Sequence
        (B) LOCATION: 434...1843

(xi) SEQUENCE DESCRIPTION: SEQ ID NO:1:

```
GGAATTCCGG GCGCAGGCCG GGACTCCGCG CCACGGCAGC CAGTCTCACC TGGCGGCACC      60
```

-continued

```
GCCCGCCCAC CGCCCCGGCC ACAGCCCCTG CGCCCACGGC AGCACTCGAG GCGACCGCGA    120

CAGTGGTGGG GGACGCTGCT GAGTGGAAGA GAGCGCAGCC GGCCACCGGA CCTACTTACT    180

CGCCTTGCTG ATTGTCTATT TTTGCGTTTA CAACTTTTCT AAGAACTTTT GTATACAAAG    240

GAACTTTTTA AAAAGACGC TTCCAAGTTA TATTTAATCC AAAGAAGAAG GATCTCGGCC     300

AATTTGGGGT TTTGGGTTTT GGCTTCGTTT CTTCTCTTCG TTGACTTTGG GGTTCAGGTG    360

CCCCAGCTGC TTCGGGCTGC CGAGGACCTT CTGGGCCCCC ACATTAATGA GGCAGCCACC    420

TGGCGAGTCT GAC ATG GCT GTC AGC GAC GCG CTG CTC CCA TCT TTC TCC      469
            Met Ala Val Ser Asp Ala Leu Leu Pro Ser Phe Ser
              1               5                  10

ACG TTC GCG TCT GGC CCG GCG GGA AGG GAG AAG ACA CTG CGT CAA GCA     517
Thr Phe Ala Ser Gly Pro Ala Gly Arg Glu Lys Thr Leu Arg Gln Ala
         15                  20                  25

GGT GCC CCG AAT AAC CGC TGG CGG GAG GAG CTC TCC CAC ATG AAG CGA     565
Gly Ala Pro Asn Asn Arg Trp Arg Glu Glu Leu Ser His Met Lys Arg
 30                  35                  40

CTT CCC CCA GTG CTT CCC GCC GGC CCC TAT GAC CTG GCG GCG GCG ACC     613
Leu Pro Pro Val Leu Pro Ala Gly Pro Tyr Asp Leu Ala Ala Ala Thr
 45                  50                  55                  60

GTG GCC ACA GAC CTG GAG AGC GCC GGA GCC GGT GCG GCT TGC GGC GGT     661
Val Ala Thr Asp Leu Glu Ser Ala Gly Ala Gly Ala Ala Cys Gly Gly
             65                  70                  75

AGC AAC CTG GCG CCC CTA CCT CGG AGA GAG ACC GAG GAG TTC AAC GAT     709
Ser Asn Leu Ala Pro Leu Pro Arg Arg Glu Thr Glu Glu Phe Asn Asp
             80                  85                  90

CTC CTG GAC CTG GAC TTT ATT CTC TCC AAT TCG CTG ACC CAT CCT CCG     757
Leu Leu Asp Leu Asp Phe Ile Leu Ser Asn Ser Leu Thr His Pro Pro
             95                  100                 105

GAG TCA GTG GCC GCC ACC GTG TCC TCG TCA GCG TCA GCC TCC TCT TCG     805
Glu Ser Val Ala Ala Thr Val Ser Ser Ser Ala Ser Ala Ser Ser Ser
    110                 115                 120

TCG TCG CCG TCG AGC AGC GGC CCT GCC AGC GCG CCC TCC ACC TGC AGC     853
Ser Ser Pro Ser Ser Ser Gly Pro Ala Ser Ala Pro Ser Thr Cys Ser
125                 130                 135                 140

TTC ACC TAT CCG ATC CGG GCC GGG AAC GAC CCG GGC GTG GCG CCG GGC     901
Phe Thr Tyr Pro Ile Arg Ala Gly Asn Asp Pro Gly Val Ala Pro Gly
                145                 150                 155

GGC ACG GGC GGA GGC CTC CTC TAT GGC AGG GAG TCC GCT CCC CCT CCG     949
Gly Thr Gly Gly Gly Leu Leu Tyr Gly Arg Glu Ser Ala Pro Pro Pro
            160                 165                 170

ACG GCT CCC TTC AAC CTG GCG GAC ATC AAC GAC GTG AGC CCC TCG GGC     997
Thr Ala Pro Phe Asn Leu Ala Asp Ile Asn Asp Val Ser Pro Ser Gly
        175                 180                 185

GGC TTC GTG GCC GAG CTC CTG CGG CCA GAA TTG GAC CCG GTG TAC ATT    1045
Gly Phe Val Ala Glu Leu Leu Arg Pro Glu Leu Asp Pro Val Tyr Ile
    190                 195                 200

CCG CCG CAG CAG CCG CAG CCG CCA GGT GGC GGG CTG ATG GGC AAG TTC    1093
Pro Pro Gln Gln Pro Gln Pro Pro Gly Gly Gly Leu Met Gly Lys Phe
205                 210                 215                 220

GTG CTG AAG GCG TCG CTG AGC GCC CCT GGC AGC GAG TAC GGC AGC CCG    1141
Val Leu Lys Ala Ser Leu Ser Ala Pro Gly Ser Glu Tyr Gly Ser Pro
                225                 230                 235

TCG GTC ATC AGC GTC ACG AAA GGC AGC CCT GAC GGC AGC CAC CCG GTG    1189
Ser Val Ile Ser Val Thr Lys Gly Ser Pro Asp Gly Ser His Pro Val
            240                 245                 250

GTG GTG GCG CCC TAC AAC GGC GGG CCG CCG CGC ACG TGC CCC AAG ATC    1237
Val Val Ala Pro Tyr Asn Gly Gly Pro Pro Arg Thr Cys Pro Lys Ile
```

-continued

```
            255                 260                 265
AAG CAG GAG GCG GTC TCT TCG TGC ACC CAC TTG GGC GCT GGA CCC CCT      1285
Lys Gln Glu Ala Val Ser Ser Cys Thr His Leu Gly Ala Gly Pro Pro
        270                 275                 280

CTC AGC AAT GGC CAC CGG CCG GCT GCA CAC GAC TTC CCC CTG GGG CGG      1333
Leu Ser Asn Gly His Arg Pro Ala Ala His Asp Phe Pro Leu Gly Arg
285                 290                 295                 300

CAG CTC CCC AGC AGG ACT ACC CCG ACC CTG GGT CTT GAG GAA GTG CTG      1381
Gln Leu Pro Ser Arg Thr Thr Pro Thr Leu Gly Leu Glu Glu Val Leu
                305                 310                 315

AGC AGC AGG GAC TGT CAC CCT GCC CTG CCG CTT CCT CCC GGC TTC CAT      1429
Ser Ser Arg Asp Cys His Pro Ala Leu Pro Leu Pro Pro Gly Phe His
            320                 325                 330

CCC CAC CCG GGG CCC AAT TAC CCA TCC TTC CTG CCC GAT CAG ATG CAG      1477
Pro His Pro Gly Pro Asn Tyr Pro Ser Phe Leu Pro Asp Gln Met Gln
        335                 340                 345

CCG CAA GTC CCG CCG CTC CAT TAC CAA GAG CTC ATG CCA CCC GGT TCC      1525
Pro Gln Val Pro Pro Leu His Tyr Gln Glu Leu Met Pro Pro Gly Ser
350                 355                 360

TGC ATG CCA GAG GAG CCC AAG CCA AAG AGG GGA AGA CGA TCG TGG CCC      1573
Cys Met Pro Glu Glu Pro Lys Pro Lys Arg Gly Arg Arg Ser Trp Pro
365                 370                 375                 380

CGG AAA AGG ACC GCC ACC CAC ACT TGT GAT TAC GCG GGC TGC GGC AAA      1621
Arg Lys Arg Thr Ala Thr His Thr Cys Asp Tyr Ala Gly Cys Gly Lys
                385                 390                 395

ACC TAC ACA AAG AGT TCC CAT CTC AAG GCA CAC CTG CGA ACC CAC ACA      1669
Thr Tyr Thr Lys Ser Ser His Leu Lys Ala His Leu Arg Thr His Thr
            400                 405                 410

GGT GAG AAA CCT TAC CAC TGT GAC TGG GAC GGC TGT GGA TGG AAA TTC      1717
Gly Glu Lys Pro Tyr His Cys Asp Trp Asp Gly Cys Gly Trp Lys Phe
        415                 420                 425

GCC CGC TCA GAT GAA CTG ACC AGG CAC TAC CGT AAA CAC ACG GGG CAC      1765
Ala Arg Ser Asp Glu Leu Thr Arg His Tyr Arg Lys His Thr Gly His
    430                 435                 440

CGC CCG TTC CAG TGC CAA AAA TGC GAC CGA GCA TTT TCC AGG TCG GAC      1813
Arg Pro Phe Gln Cys Gln Lys Cys Asp Arg Ala Phe Ser Arg Ser Asp
445                 450                 455                 460

CAC CTC GCC TTA CAC ATG AAG AGG CAT TTT TAAATCCCAG ACAGTGGATA TGA    1866
His Leu Ala Leu His Met Lys Arg His Phe
                465                 470

CCCACACTGC CAGAAGAGAA TTC                                            1889
```

(2) INFORMATION FOR SEQ ID NO:2:

(i) SEQUENCE CHARACTERISTICS:
        (A) LENGTH: 470 amino acids
        (B) TYPE: amino acid
        (D) TOPOLOGY: linear     (ii) MOLECULE TYPE: protein     (v) FRAGMENT TYPE: internal     (xi) SEQUENCE DESCRIPTION: SEQ ID NO:2:

```
Met Ala Val Ser Asp Ala Leu Leu Pro Ser Phe Ser Thr Phe Ala Ser
 1               5                  10                  15

Gly Pro Ala Gly Arg Glu Lys Thr Leu Arg Gln Ala Gly Ala Pro Asn
                20                  25                  30

Asn Arg Trp Arg Glu Glu Leu Ser His Met Lys Arg Leu Pro Pro Val
            35                  40                  45
```

-continued

```
Leu Pro Ala Gly Pro Tyr Asp Leu Ala Ala Thr Val Ala Thr Asp
     50                  55                  60

Leu Glu Ser Ala Gly Ala Ala Cys Gly Gly Ser Asn Leu Ala
 65              70              75                  80

Pro Leu Pro Arg Arg Glu Thr Glu Phe Asn Asp Leu Leu Asp Leu
             85              90              95

Asp Phe Ile Leu Ser Asn Ser Leu Thr His Pro Pro Glu Ser Val Ala
            100                 105                 110

Ala Thr Val Ser Ser Ser Ala Ser Ala Ser Ser Ser Ser Pro Ser
            115                 120                 125

Ser Ser Gly Pro Ala Ser Ala Pro Ser Thr Cys Ser Phe Thr Tyr Pro
        130                 135                 140

Ile Arg Ala Gly Asn Asp Pro Gly Val Ala Pro Gly Gly Thr Gly Gly
145                 150                 155                 160

Gly Leu Leu Tyr Gly Arg Glu Ser Ala Pro Pro Thr Ala Pro Phe
                165                 170                 175

Asn Leu Ala Asp Ile Asn Asp Val Ser Pro Ser Gly Gly Phe Val Ala
            180                 185                 190

Glu Leu Leu Arg Pro Glu Leu Asp Pro Val Tyr Ile Pro Pro Gln Gln
                195                 200                 205

Pro Gln Pro Pro Gly Gly Gly Leu Met Gly Lys Phe Val Leu Lys Ala
        210                 215                 220

Ser Leu Ser Ala Pro Gly Ser Glu Tyr Gly Ser Pro Ser Val Ile Ser
225                 230                 235                 240

Val Thr Lys Gly Ser Pro Asp Gly Ser His Pro Val Val Ala Pro
                245                 250                 255

Tyr Asn Gly Gly Pro Pro Arg Thr Cys Pro Lys Ile Lys Gln Glu Ala
                260                 265                 270

Val Ser Ser Cys Thr His Leu Gly Ala Gly Pro Pro Leu Ser Asn Gly
            275                 280                 285

His Arg Pro Ala Ala His Asp Phe Pro Leu Gly Arg Gln Leu Pro Ser
    290                 295                 300

Arg Thr Thr Pro Thr Leu Gly Leu Glu Glu Val Leu Ser Ser Arg Asp
305                 310                 315                 320

Cys His Pro Ala Leu Pro Leu Pro Pro Gly Phe His Pro His Pro Gly
                325                 330                 335

Pro Asn Tyr Pro Ser Phe Leu Pro Asp Gln Met Gln Pro Gln Val Pro
                340                 345                 350

Pro Leu His Tyr Gln Glu Leu Met Pro Pro Gly Ser Cys Met Pro Glu
            355                 360                 365

Glu Pro Lys Pro Lys Arg Gly Arg Arg Ser Trp Pro Arg Lys Arg Thr
    370                 375                 380

Ala Thr His Thr Cys Asp Tyr Ala Gly Cys Gly Lys Thr Tyr Thr Lys
385                 390                 395                 400

Ser Ser His Leu Lys Ala His Leu Arg Thr His Thr Gly Glu Lys Pro
                405                 410                 415

Tyr His Cys Asp Trp Asp Gly Cys Gly Trp Lys Phe Ala Arg Ser Asp
                420                 425                 430

Glu Leu Thr Arg His Tyr Arg Lys His Thr Gly His Arg Pro Phe Gln
            435                 440                 445

Cys Gln Lys Cys Asp Arg Ala Phe Ser Arg Ser Asp His Leu Ala Leu
    450                 455                 460

His Met Lys Arg His Phe
```

```
465                 470
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (xi) SEQUENCE DESCRIPTION: SEQ ID NO:3:

```
GAACTTTGGC ACCTAAGAGG CAG                                           23
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (xi) SEQUENCE DESCRIPTION: SEQ ID NO:4:

```
ACGCTTCATG TGCAGAGCTA AGTG                                          24
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (xi) SEQUENCE DESCRIPTION: SEQ ID NO:5:

```
AGCTAGCCAC ACCCTGAAGC T                                             21
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (xi) SEQUENCE DESCRIPTION: SEQ ID NO:6:

```
AGCTAGCCAC ACCGTGAAGC T                                             21
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (xi) SEQUENCE DESCRIPTION: SEQ ID NO:7:

```
GACCGTGGCA CAGACTGGAG                                               20
```

(2) INFORMATION FOR SEQ ID NO:8:

(i) SEQUENCE CHARACTERISTICS:
        (A) LENGTH: 1889 base pairs
        (B) TYPE: nucleic acid
        (C) STRANDEDNESS: single
        (D) TOPOLOGY: linear     (ix) FEATURE:
        (A) NAME/KEY: Coding Sequence
        (B) LOCATION: 407...1843

(xi) SEQUENCE DESCRIPTION: SEQ ID NO:8:

```
GGAATTCCGG GCGCAGGCCG GGACTCCGCG CCACGGCAGC CAGTCTCACC TGGCGGCACC      60

GCCCGCCCAC CGCCCCGGCC ACAGCCCCTG CGCCCACGGC AGCACTCGAG GCGACCGCGA     120

CAGTGGTGGG GGACGCTGCT GAGTGGAAGA GAGCGCAGCC GGCCACCGGA CCTACTTACT     180

CGCCTTGCTG ATTGTCTATT TTTGCGTTTA CAACTTTTCT AAGAACTTTT GTATACAAAG     240

GAACTTTTTA AAAAGACGC TTCCAAGTTA TATTTAATCC AAAGAAGAAG GATCTCGGCC      300

AATTTGGGGT TTTGGGTTTT GGCTTCGTTT CTTCTCTTCG TTGACTTTGG GGTTCAGGTG    360

CCCCAGCTGC TTCGGGCTGC CGAGGACCTT CTGGGCCCCC ACATTA ATG AGG CAG         415
                                                  Met Arg Gln
                                                   1
```

| | | |
|---|---|---|
| CCA CCT GGC GAG TCT GAC ATG GCT GTC AGC GAC GCG CTG CTC CCA TCT | 463 | |
| Pro Pro Gly Glu Ser Asp Met Ala Val Ser Asp Ala Leu Leu Pro Ser | | |
| 5              10              15 | | |

```
TTC TCC ACG TTC GCG TCT GGC CCG GCG GGA AGG GAG AAG ACA CTG CGT      511
Phe Ser Thr Phe Ala Ser Gly Pro Ala Gly Arg Glu Lys Thr Leu Arg
 20              25              30              35

CAA GCA GGT GCC CCG AAT AAC CGC TGG CGG GAG GAG CTC TCC CAC ATG      559
Gln Ala Gly Ala Pro Asn Asn Arg Trp Arg Glu Glu Leu Ser His Met
         40              45              50

AAG CGA CTT CCC CCA GTG CTT CCC GCC GGC CCC TAT GAC CTG GCG GCG      607
Lys Arg Leu Pro Pro Val Leu Pro Ala Gly Pro Tyr Asp Leu Ala Ala
             55              60              65

GCG ACC GTG GCC ACA GAC CTG GAG AGC GCC GGA GCC GGT GCG GCT TGC      655
Ala Thr Val Ala Thr Asp Leu Glu Ser Ala Gly Ala Gly Ala Ala Cys
         70              75              80

GGC GGT AGC AAC CTG GCG CCC CTA CCT CGG AGA GAG ACC GAG GAG TTC      703
Gly Gly Ser Asn Leu Ala Pro Leu Pro Arg Arg Glu Thr Glu Glu Phe
 85              90              95

AAC GAT CTC CTG GAC CTG GAC TTT ATT CTC TCC AAT TCG CTG ACC CAT      751
Asn Asp Leu Leu Asp Leu Asp Phe Ile Leu Ser Asn Ser Leu Thr His
100             105             110             115

CCT CCG GAG TCA GTG GCC GCC ACC GTG TCC TCG TCA GCG TCA GCC TCC      799
Pro Pro Glu Ser Val Ala Ala Thr Val Ser Ser Ser Ala Ser Ala Ser
             120             125             130

TCT TCG TCG TCG CCG TCG AGC AGC GGC CCT GCC AGC GCG CCC TCC ACC      847
Ser Ser Ser Ser Pro Ser Ser Ser Gly Pro Ala Ser Ala Pro Ser Thr
         135             140             145

TGC AGC TTC ACC TAT CCG ATC CGG GCC GGG AAC GAC CCG GGC GTG GCG      895
Cys Ser Phe Thr Tyr Pro Ile Arg Ala Gly Asn Asp Pro Gly Val Ala
             150             155             160

CCG GGC GGC ACG GGC GGA GGC CTC CTC TAT GGC AGG GAG TCC GCT CCC      943
Pro Gly Gly Thr Gly Gly Gly Leu Leu Tyr Gly Arg Glu Ser Ala Pro
 165             170             175

CCT CCG ACG GCT CCC TTC AAC CTG GCG GAC ATC AAC GAC GTG AGC CCC      991
Pro Pro Thr Ala Pro Phe Asn Leu Ala Asp Ile Asn Asp Val Ser Pro
180             185             190             195

TCG GGC GGC TTC GTG GCC GAG CTC CTG CGG CCA GAA TTG GAC CCG GTG     1039
Ser Gly Gly Phe Val Ala Glu Leu Leu Arg Pro Glu Leu Asp Pro Val
             200             205             210

TAC ATT CCG CCG CAG CAG CCG CAG CCG CCA GGT GGC GGG CTG ATG GGC     1087
Tyr Ile Pro Pro Gln Gln Pro Gln Pro Pro Gly Gly Gly Leu Met Gly
         215             220             225

AAG TTC GTG CTG AAG GCG TCG CTG AGC GCC CCT GGC AGC GAG TAC GGC     1135
Lys Phe Val Leu Lys Ala Ser Leu Ser Ala Pro Gly Ser Glu Tyr Gly
             230             235             240
```

```
AGC CCG TCG GTC ATC AGC GTC ACG AAA GGC AGC CCT GAC GGC AGC CAC      1183
Ser Pro Ser Val Ile Ser Val Thr Lys Gly Ser Pro Asp Gly Ser His
    245                 250                 255

CCG GTG GTG GTG GCG CCC TAC AAC GGC GGG CCG CCG CGC ACG TGC CCC      1231
Pro Val Val Val Ala Pro Tyr Asn Gly Gly Pro Pro Arg Thr Cys Pro
260                 265                 270                 275

AAG ATC AAG CAG GAG GCG GTC TCT TCG TGC ACC CAC TTG GGC GCT GGA      1279
Lys Ile Lys Gln Glu Ala Val Ser Ser Cys Thr His Leu Gly Ala Gly
                280                 285                 290

CCC CCT CTC AGC AAT GGC CAC CGG CCG GCT GCA CAC GAC TTC CCC CTG      1327
Pro Pro Leu Ser Asn Gly His Arg Pro Ala Ala His Asp Phe Pro Leu
            295                 300                 305

GGG CGG CAG CTC CCC AGC AGG ACT ACC CCG ACC CTG GGT CTT GAG GAA      1375
Gly Arg Gln Leu Pro Ser Arg Thr Thr Pro Thr Leu Gly Leu Glu Glu
        310                 315                 320

GTG CTG AGC AGC AGG GAC TGT CAC CCT GCC CTG CCG CTT CCT CCC GGC      1423
Val Leu Ser Ser Arg Asp Cys His Pro Ala Leu Pro Leu Pro Pro Gly
    325                 330                 335

TTC CAT CCC CAC CCG GGG CCC AAT TAC CCA TCC TTC CTG CCC GAT CAG      1471
Phe His Pro His Pro Gly Pro Asn Tyr Pro Ser Phe Leu Pro Asp Gln
340                 345                 350                 355

ATG CAG CCG CAA GTC CCG CCG CTC CAT TAC CAA GAG CTC ATG CCA CCC      1519
Met Gln Pro Gln Val Pro Pro Leu His Tyr Gln Glu Leu Met Pro Pro
                360                 365                 370

GGT TCC TGC ATG CCA GAG GAG CCC AAG CCA AAG AGG GGA AGA CGA TCG      1567
Gly Ser Cys Met Pro Glu Glu Pro Lys Pro Lys Arg Gly Arg Arg Ser
            375                 380                 385

TGG CCC CGG AAA AGG ACC GCC ACC CAC ACT TGT GAT TAC GCG GGC TGC      1615
Trp Pro Arg Lys Arg Thr Ala Thr His Thr Cys Asp Tyr Ala Gly Cys
        390                 395                 400

GGC AAA ACC TAC ACA AAG AGT TCC CAT CTC AAG GCA CAC CTG CGA ACC      1663
Gly Lys Thr Tyr Thr Lys Ser Ser His Leu Lys Ala His Leu Arg Thr
    405                 410                 415

CAC ACA GGT GAG AAA CCT TAC CAC TGT GAC TGG GAC GGC TGT GGA TGG      1711
His Thr Gly Glu Lys Pro Tyr His Cys Asp Trp Asp Gly Cys Gly Trp
420                 425                 430                 435

AAA TTC GCC CGC TCA GAT GAA CTG ACC AGG CAC TAC CGT AAA CAC ACG      1759
Lys Phe Ala Arg Ser Asp Glu Leu Thr Arg His Tyr Arg Lys His Thr
                440                 445                 450

GGG CAC CGC CCG TTC CAG TGC CAA AAA TGC GAC CGA GCA TTT TCC AGG      1807
Gly His Arg Pro Phe Gln Cys Gln Lys Cys Asp Arg Ala Phe Ser Arg
            455                 460                 465

TCG GAC CAC CTC GCC TTA CAC ATG AAG AGG CAT TTT TAAATCCCAG ACAGTG    1859
Ser Asp His Leu Ala Leu His Met Lys Arg His Phe
        470                 475

GATATGACCC ACACTGCCAG AAGAGAATTC                                     1889
```

(2) INFORMATION FOR SEQ ID NO:9:

(i) SEQUENCE CHARACTERISTICS:
        (A) LENGTH: 479 amino acids
        (B) TYPE: amino acid
        (D) TOPOLOGY: linear     (ii) MOLECULE TYPE: protein     (v) FRAGMENT TYPE: internal     (xi) SEQUENCE DESCRIPTION: SEQ ID NO:9:

```
Met Arg Gln Pro Pro Gly Glu Ser Asp Met Ala Val Ser Asp Ala Leu
1               5                   10                  15
```

```
Leu Pro Ser Phe Ser Thr Phe Ala Ser Gly Pro Ala Gly Arg Glu Lys
             20                  25                  30

Thr Leu Arg Gln Ala Gly Ala Pro Asn Asn Arg Trp Arg Glu Glu Leu
         35                  40                  45

Ser His Met Lys Arg Leu Pro Pro Val Leu Pro Ala Gly Pro Tyr Asp
     50                  55                  60

Leu Ala Ala Ala Thr Val Ala Thr Asp Leu Glu Ser Ala Gly Ala Gly
 65                  70                  75                  80

Ala Ala Cys Gly Gly Ser Asn Leu Ala Pro Leu Pro Arg Arg Glu Thr
                 85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Thr Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
```

```
                435                 440                 445
Lys His Thr Gly His Arg Pro Phe Gln Cys Gln Lys Cys Asp Arg Ala
            450                 455                 460
Phe Ser Arg Ser Asp His Leu Ala Leu His Met Lys Arg His Phe
465                 470                 475
```

(2) INFORMATION FOR SEQ ID NO:10:

(i) SEQUENCE CHARACTERISTICS:
        (A) LENGTH: 13 amino acids
        (B) TYPE: amino acid
        (D) TOPOLOGY: linear     (ii) MOLECULE TYPE: peptide     (xi) SEQUENCE DESCRIPTION: SEQ ID NO:10:

```
Gly His Glu Ser Ser Ala Ser Asp Arg Cys Gly Leu Pro
1               5                  10
```

(2) INFORMATION FOR SEQ ID NO:11:

(i) SEQUENCE CHARACTERISTICS:
        (A) LENGTH: 7 amino acids
        (B) TYPE: amino acid
        (D) TOPOLOGY: linear     (ii) MOLECULE TYPE: peptide     (xi) SEQUENCE DESCRIPTION: SEQ ID NO:11:

```
Ser Thr Asn Asn Glu His Leu
1               5
```

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: linear     (ii) MOLECULE TYPE: peptide     (xi) SEQUENCE DESCRIPTION: SEQ ID NO:12:

```
Pro Thr Val Lys Thr Glu Asp Arg Ala Lys Gly Val Asn Ser
1               5                  10
```

(2) INFORMATION FOR SEQ ID NO:13:

(i) SEQUENCE CHARACTERISTICS:
        (A) LENGTH: 34 amino acids
        (B) TYPE: amino acid
        (D) TOPOLOGY: linear     (ii) MOLECULE TYPE: peptide     (xi) SEQUENCE DESCRIPTION: SEQ ID NO:13:

```
His Ile Gln Val Gly Thr Arg Trp Arg Phe Met Thr Ser Tyr Lys Arg
1               5                  10                  15
Thr Gln Lys Thr Glu Lys Lys Ala Pro Glu Pro Lys Arg Met Ser Lys
            20                  25                  30
Ile Thr
```